(12) United States Patent
Kubo et al.

(10) Patent No.: US 7,838,494 B2
(45) Date of Patent: Nov. 23, 2010

(54) DIFFERENTIATION- OR REGENERATION-INDUCING AGENT FOR ALVEOLI

(75) Inventors: Hiroshi Kubo, Miyagi (JP); Kota Ishizawa, Miyagi (JP); Hidetada Sasaki, Miyagi (JP); Toshikazu Nakamura, Kyoto (JP)

(73) Assignees: Tohoku Technoarch Co., Ltd., Miiyagi (JP); Kringle Pharma Inc., Osaka (JP)

( * ) Notice: Subject to any disclaimer, the term of this patent is extended or adjusted under 35 U.S.C. 154(b) by 163 days.

(21) Appl. No.: 10/592,087

(22) PCT Filed: Mar. 7, 2005

(86) PCT No.: PCT/JP2005/004384

§ 371 (c)(1),
(2), (4) Date: Nov. 20, 2006

(87) PCT Pub. No.: WO2005/084698

PCT Pub. Date: Sep. 15, 2005

(65) Prior Publication Data

US 2007/0197433 A1     Aug. 23, 2007

(30) Foreign Application Priority Data

Mar. 9, 2004     (JP) .............................. 2004-066410

(51) Int. Cl.
*A61K 38/18*     (2006.01)
*C07K 14/475*   (2006.01)

(52) U.S. Cl. .......................... 514/12; 530/350; 530/399

(58) Field of Classification Search .................. None
See application file for complete search history.

(56) References Cited

U.S. PATENT DOCUMENTS 5,888,965 A     3/1999     Kmiecik et al.

FOREIGN PATENT DOCUMENTS

| JP | 6172207 | 6/1994 |
|----|---------|--------|
| JP | 8268906 | 10/1996 |

OTHER PUBLICATIONS

Y. Sakamaki et al., "Hepatocyte Growth Factor Stimulates Proliferation of Respiratory Epithelial Cells during Postpneumonectomy Compensatory Lung Growth in Mice", American Journal of Respiratory Cell and Molecular Biology, vol. 26, No. 5, pp. 525-533, May 2002.

R. J. Mason et al., "Hepatocyte Growth Factor: The Key to Alveolar Septation?", American Journal of Respiratory Cell and Molecular Biology, vol. 26, No. 5, pp. 517-520, May 2002.

L. B. Ware et al., "Keratinocyte and Hepatocyte Growth Factors in the Lung: Roles in Lung Development, Inflammation, and Repair", American Journal of Physiology, vol. 282, No. 5 Part 1, pp. L924-L940, May 2002.

K. Ishizawa et al., "Hepatocyte Growth Factor Induces Angiogenesis in Injured Lungs Through Mobilizing Endothelial Progenitor Cells", Biochemical and Biophysical Research Communications, vol. 324, No. 1, pp. 276-280, Nov. 5, 2004.

M. Dohi et al., "Hepatocyte Growth Factor Attenuates Collagen Accumulation in a Murine Model of Pulmonary Fibrosis," *Am. J Respir. Crit. Care Med.* (2000), vol. 162, No. 6, pp. 2302-2307.

K. Akiyama et al., "Effect of Hepatocyte Growth Factor on Lung Injury and Development of Clinical Application," *Chest* (2001), vol. 120, No. SUPPL, p. 59S.

X. Liu et al., "The protective effect of hepatocyte growth-promoting factor (pHGF) against hydrogen peroxide-induced acute lung injury in rats," *Med. Electron. Microse.* (2001), vol. 34, pp. 92-102.

*Primary Examiner*—Marianne P Allen
(74) *Attorney, Agent, or Firm*—Wenderoth, Lind & Ponack, L.L.P.

(57) ABSTRACT

The present invention provides an agent comprising HGF for inducing differentiation of bone marrow cells into alveolar cells. The present invention also provides an HGF-containing agent for alveolar formation in pulmonary emphysema and the like in which alveoli are destroyed.

9 Claims, 2 Drawing Sheets

DIFFERENTIATION- OR REGENERATION-INDUCING AGENT FOR ALVEOLI

This application is a U.S. national stage of International Application No. PCT/JP2005/004384 filed Mar. 7, 2005.

TECHNICAL FIELD

The present invention relates to an agent comprising hepatocyte growth factor as an active ingredient for inducing differentiation of bone marrow cells into alveolar cells, and also relates to an agent for forming alveoli by such differentiation induction.

BACKGROUND ART

Hepatocyte growth factor (hereinafter referred to as HGF) was originally identified as a growth factor for mature hepatocytes, and its gene (cDNA) was cloned in 1989 (see non-patent literatures 1 and 2).

It has been revealed so far that HGF exerts various biological activities such as cell proliferation, promotion of cell migration, morphogenesis induction, cell death inhibition and the like on various cells as well as hepatocytes (see non-patent literatures 3 to 6).

The biological activities of HGF are expressed via its receptor, i.e. c-Met tyrosine kinase. HGF has various biological activities and has functions of repairing and protecting various tissues from various injuries.

Angiogenesis promoting activity is one of HGF functions of regeneration or protection of tissues. HGF not only promotes proliferation and migration of vascular endothelial cells, but also shows in vivo potent angiogenesis-inducing activity (see non-patent literatures 7 to 10).

Further, HGF has an activity of inhibiting cell death of vascular endothelial cells (see non-patent literatures 11 to 13).

Lung is an organ composed of a large number of alveoli. The air taken into the body by respiration is passed through trachea and then enters into bronchi. Bronchi are further branched, and one bronchiole is connected to one alveolus. Human alveolus is a small sac of about 0.2 mm diameter, and is surrounded by capillaries. Gas exchange takes place in the alveoli, i.e., oxygen is taken from the inspired gas entered through the bronchi into the alveoli, and carbon dioxide in the blood is exhausted into the alveoli as expired gas. Pulmonary emphysema is physiologically a progressive destruction of the alveoli, and the surface area of alveoli available for gas exchange is reduced as disease progresses. Inadequate gas exchange in the alveoli causes a shortage of oxygen in the blood. With the progress of the disease, lung elasticity is lowered, resulting in respiratory difficulty. In addition, since adult lung is an organ which cannot spontaneously grow or regenerate itself, pulmonary emphysema is considered to be a progressive and irreversible disease. Massaro et. al reported that treatment with all-trans-retinoic acid (ATRA) anatomically and physiologically regenerated lung in an animal model of pulmonary emphysema (see non-patent literature 14). Further, ATRA is known to activate genes involved in lung development and to promote alveolar septation and growth of lung. However, clinical trials using ATRA failed to show significant improvement in lung structure or lung function in pulmonary emphysema patients (see non-patent literature 15).

It has been reported that HGF promotes the growth of alveolar epithelial type II cells or bronchial epithelial cells, and that HGF is involved in the repair of alveolar epithelial cells (see non-patent literatures 16-19). Also, a study on the effect of HGF on acute lung injury revealed that HGF is newly produced in the lung after injury, and that when HGF is administered to animals with an injured lung, cell proliferation in the lung tissue is stimulated and repair of the injured lung is promoted (see patent literature 2).

However, any of the above-mentioned literatures does not describe that HGF induces differentiation of bone marrow cells into alveolar cells and that regeneration or formation of alveoli is promoted by such differentiation induction.

[Patent literature 1] JP-A-89869/1996
[Patent literature 2] JP-A-172207/1994
[Non-patent literature 1] Biochemical and Biophysical Research Communications, 1984, vol. 122, p. 1450-1459
[Non-patent literature 2] Nature, 1989, vol. 342, p. 440-443
[Non-patent literature 3] The Journal of Cell Biology, 1985, vol. 129, p. 1177-1185
[Non-patent literature 4] The Journal of Biochemistry, 1986, vol. 119, p. 591-600
[Non-patent literature 5] International Review of Cytology), 1999, vol. 186, p. 225-260
[Non-patent literature 6] Kidney International, 2001, vol. 59, p. 2023-2038
[Non-patent literature 7] The Journal of Cell Biology, 1992, vol. 119, p. 629-641
[Non-patent literature 8] Proceedings of the National Academy of Sciences of the United States of America, 1993, vol. 90, p. 1937-1941
[Non-patent literature 9] Circulation, 1998, vol. 97, p. 381-390
[Non-patent literature 10] Hypertension, 1999, vol. 33, p. 1379-1384
[Non-patent literature 11] Journal of Hypertension, 2000, vol. 18, p. 1411-1420
[Non-patent literature 12] Hypertension, 2001, vol. 37, p. 581-586
[Non-patent literature 13] Diabetes, 2002, vol. 51, p. 2604-2611
[Non-patent literature 14] Massaro, G. D., et. al, Nature Medicine, 1997, vol. 3, p. 675-677
[Non-patent literature 15] Mao, J. T., et. al, American Journal of Respiratory & Critical Care Medicine, 2002, vol. 165, p. 718-723
[Non-patent literature 16] Mason R J, et. al, American Journal of Respiratory Cell and Molecular Biology, 1994, vol. 11, p. 561-567
[Non-patent literature 17] Shiratori M, et. al, American Journal of Respiratory Cell and Molecular Biology, 1995, vol. 12, p. 171-180
[Non-patent literature 18] Ohmichi H, et. al, The American Journal of Physiology, 1996, vol. 270, p. L1031-L1039
[Non-patent literature 19] Sakamaki, Y, et. al, American Journal of Respiratory Cell and Molecular Biology, 2002, vol. 26, p. 525-533.

DISCLOSURE OF INVENTION

An object of the present invention is to provide an agent for inducing differentiation of bone marrow cells into alveolar cells. Another object of the present invention is to utilize the above differentiation-inducing agent as an agent for promoting regeneration of damaged alveoli or alveolar formation.

The present inventors have newly found that damaged alveoli observed in, for example, pulmonary emphysema are regenerable, the regenerated alveoli are differentiated from bone marrow cells, and HGF induces such differentiation. As a result of extensive studies based on these findings, the present inventors have completed the present invention.

Namely, the present invention relates to:
(1) An agent for inducing differentiation of bone marrow cells into alveolar cells comprising hepatocyte growth factor,
(2) The differentiation-inducing agent according to the above (1), wherein the alveolar cells are alveolar epithelial cells, and
(3) The differentiation-inducing agent according to the above (1) or (2), which is an agent for promoting alveolar regeneration or formation.

Also, the present invention relates to a method for inducing differentiation of bone marrow cells into alveolar cells by administration of HGF to mammals, and further relates to the use of HGF to produce medicines for inducing differentiation of bone marrow cells into alveolar cells. Further, the present invention relates to a method for culturing bone marrow cells together with a differentiation-inducing agent containing HGF, and transplanting the alveolar cells differentiated from the bone marrow cells to mammals, or a method for culturing bone marrow cells, transplanting the proliferated bone marrow cells to mammals, administering simultaneously a differentiation-inducing agent containing HGF, and inducing differentiation of the transplanted bone marrow cells into alveolar cells. Furthermore, the present invention includes a gene therapy for regeneration of damaged alveoli or new alveolar formation comprising introduction of HGF gene as well as administration of HGF.

Since the differentiation-inducing agent of the present invention induces differentiation of bone marrow cells into alveolar cells, new alveoli can be formed in a disease in which alveoli are destroyed such as pulmonary emphysema, pulmonary fibrosis with honey-comb lung, pulmonary lymphangiomyomatosis (LAM), destroyed lung after pulmonary resection and the like Further, when bone marrow cells are cultured in the presence of a differentiation-inducing agent of the present invention, alveolar cells differentiated from the bone marrow cells can be prepared.

Furthermore, the alveolar cells differentiated from bone marrow cells obtained by culturing bone marrow cells together with a differentiation-inducing agent of the present invention can be utilized as cells for transplantation in the field of regenerative medicine.

BEST MODE FOR CARRYING OUT THE INVENTION

Figure 1:
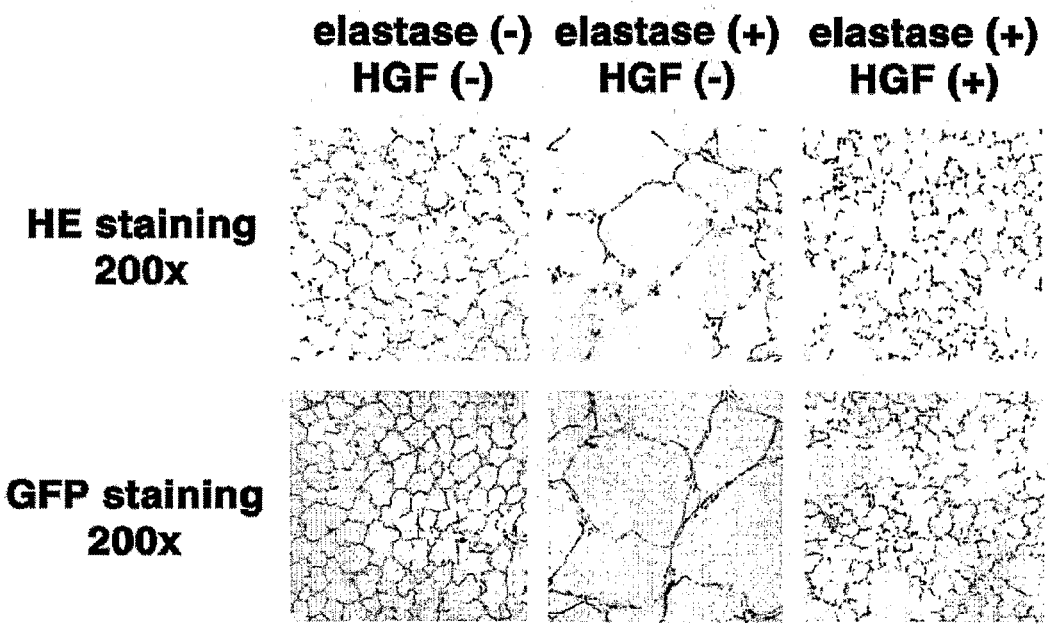
FIG. 1 shows histological findings in the lung of pulmonary emphysema-induced recipient mice.

HGF used in the present invention is a known substance. HGF prepared by various processes can be used in the present invention as long as it is purified enough to be used as a medical agent. Regarding production processes of HGF, for example, HGF can be obtained by cultivating primary culture cells or cells of an established cell line which produce HGF, isolating HGF from culture supernatant or the like and purifying the isolated HGF. Alternatively, recombinant HGF can also be obtained according to a genetic engineering technique by integrating a gene encoding HGF into an appropriate vector, inserting the vector into proper host cells for transformation thereof and collecting the target recombinant HGF from the culture supernatant of the transformed cells (see, for example, JP-A-111382/1993; Biochem. Biophys. Res. Commun., 1989, vol. 163, p. 967).

The above-mentioned host cells are not particularly limited, and various kinds of host cells conventionally used in the genetic engineering techniques, such as *Escherichia coli,* yeast, animal cells or the like may be used. The obtained HGF, so long as it has substantially the same action as natural HGF, may include substitution, deletion, addition and/or insertion of one or more (e.g., several) of amino acids in the amino acid sequence thereof. Similarly, HGF may include substitution, deletion and/or addition of sugar chain(s). Here "the deletion, substitution, addition or insertion of one or more of amino acids" in the amino acid sequence means that the amino acids in a number that can naturally occur (one to several amino acids) may be deleted, substituted, added and/or inserted into the amino acid sequence by known technical methods such as genetic engineering techniques, site-specific mutation induction and the like.

Also, "HGF including substitution, deletion and/or addition of sugar chain(s)" means, for example, (1) glycosylation-deficient HGF which is obtained by treating a natural glycosylated HGF with an enzyme to remove sugar chain(s), (2) HGF of which amino acid sequence is mutated at a glycosylation site to inhibit glycosylation, or (3) HGF of which amino acid sequence is mutated in such a manner that glycosylation occurs at a site different from the natural glycosylation site.

Further, HGF also includes a protein having at least 60% or more homology, preferably 80% or more homology, more preferably 90% or more homology, still more preferably 95% or more homology to the amino acid sequence of HGF and also having an activity to induce differentiation of bone marrow cells into alveolar cells. The above-mentioned "homology" between amino acid sequences generally means the level of homology between the amino acid residues constituting the amino acid sequences when the primary structures of the proteins are compared.

HGF used in the present invent ion may have a carboxylate (—COO⁻), amide (—CONH$_2$) or ester (—COOR) as well as a carboxyl group (—COOH) at its C terminal so long as it has substantially the same actions as natural HGF. Here, as R in the ester, optionally substituted lower alkyl groups (e.g., methyl, ethyl, propyl, cyclopentyl, benzyl, phenethyl, etc.), aryl groups (e.g., phenyl, α-naphthyl, etc.), pivaloyloxymethyl groups which are generally used as an ester for oral administration and the like may be mentioned. In addition, HGF usable in the present invention may include HGF in which an amino group of a methionine residue at the N-terminal is protected by a protective group (e.g., an acyl group such as formyl, acetyl, etc.), HGF in which a glutamyl group produced by cutting an N-terminal side in vivo has changed to a pyroglutamic acid and the like.

In the present invention, regeneration or formation of alveoli means new alveolar formation or regeneration of damaged alveoli. Alveoli are a gas exchange organ composed of alveolar epithelial cells, capillaries comprising pulmonary capillary endothelial cells, etc. and connective tissues. Further, the alveoli of the present invention include branched bronchi parts connected to the alveoli.

The differentiation-inducing agent of the present invention can be applied for the purpose of regeneration or formation of alveoli in diseases where alveoli are destroyed, such as pulmonary emphysema, pulmonary fibrosis with honey-comb lung, pulmonary lymphangiomyomatosis (LAM), destroyed lung after pulmonary resection and the like in mammals (e.g. cow, horse, pig, sheep, dog, cat) including human.

The differentiation-inducing agent of the present invention may take various dosage forms such as liquid preparations, solid preparations, capsules and the like, however, it is generally formulated with HGF alone or with a combination of HGF and a conventional carrier into injections, inhalations, suppositories or orally administrable preparations. The above-mentioned injections may be aqueous injections or oily injections.

In the case of aqueous injections, they can be prepared in such a manner that HGF is dissolved i n, for example, a solution prepared by appropriately adding a pharmaceutically acceptable carrier such as isotonic agents (e.g. sodium chloride, potassium chloride, glycerin, mannitol, sorbitol, boric acid, borax, glucose, propylene glycol, etc.), buffers (e.g. phosphoric acid buffer, acetic acid buffer, boric acid buffer, carbonic acid buffer, citric acid buffer, Tris-buffer, glutamic acid buffer, ϵ-aminocarproic acid buffer, etc.), preservatives (e.g. methyl p-oxybenzoate, ethyl p-oxybenzoate, propyl p-oxybenzoate, butyl p-oxybenzoate, chlorobutanol, benzyl alcohol, benzalkonium chloride, sodium dehydroacetate, sodium edetate, boric acid, borax, etc.), thickners (e.g. hydroxyethylcellulose, hydroxypropylcellulose, polyvinyl alcohol, polyethylene glycol, etc.), stabilizers (e.g. sodium hydrogensulfite, sodium thiosulfate, sodium edetate, sodium citrate, ascorbic acid, dibutyl hydroxy toluene, etc.), pH control agents (e.g. hydrochloric acid, sodium hydroxide, phosphoric acid, acetic acid, etc.) and the like to an aqueous solvent (e.g. injectable water, purified water, etc.), and then the solution is filtered through a filter, etc., sterilized and filled in a sterile container according to a known method. Further, appropriate solubilizers such as alcohols (e.g. ethanol, etc.), polyalcohol (e.g. propylene glycol, polyethylene glycol, etc.) or non-ionic surfactants (e.g. polysorbate 80, polyoxyethylene hydrogenated castor oil 50, etc.) may be used.

In the case of oily preparations, sesame oil, soy bean oil and the like are used as an oily solvent, and benzyl benzoate, benzyl alcohol and the like may be used as a solubilizer. The obtained injectable solution is usually filled in an ampoule or a vial. The HGF content in the injection preparation is usually adjusted to about 0.0002 to 0.2 w/v %, preferably about 0.001 to 0.1 w/v %. It is preferable that liquid preparations such as injections are preserved after removing water by freeze-preservation or freeze-drying. The freeze-dried preparation is redissolved in injectable distilled water before use.

In the case of orally administrable preparations, the dosage forms include, for example, tablets, granules, fine granules, powders, capsules, liquids, emulsions, suspensions, syrups and the like. These preparations may be prepared by the conventional method. In the case of granules or tablets, they can be produced by using pharmaceutically acceptable additives such as excipients (e.g. lactose, white sugar, glucose, starch, crystalline cellulose, etc.), lubricants (e.g. magnesium stearate, talc, stearic acid, calcium stearate, etc.), disintegrators (e.g. starch, carmellose sodium, calcium carbonate, etc.), binders (e.g. starch paste, hydroxypropyl cellulose solution, carmellose solution, gum arabic solution, gelatin solution, sodium alginate solution, etc.), and the like. Also, granules or tablets may be coated with an appropriate coating agent (e.g. gelatin, white sugar, gum arabic, carnauba wax, etc.), enteric coating agents (e.g. cellulose acetate phthalate, methacrylic acid copolymer, hydroxypropyl cellulose phthalate, carboxymethyethyl cellulose, etc.), and the like.

In the case of capsules, known excipients such as magnesium stearate, calcium stearate, talc and light anhydrous silicic acid for enhancing flowability and lubricability; crystalline cellulose or lactose for increasing flowability under pressure; and the above-mentioned disintegrators may be appropriately selected. HGF is homogeneously blended or granulated with the above-mentioned excipient, or the granules may be coated with a suitable coating agent and then filled in a capsule, or the granules may be encapsulated with a capsule base (e.g. gelatin) having increased plasticity which is endowed with addition of glycerin, sorbitol, etc. If required, coloring agents or preservatives (e.g. sulfur dioxide, methyl p-oxybenzoate, ethyl p-oxybenzoate, propyl p-oxybenzoate, butyl p-oxybenzoate, etc.) may be added to the capsule preparation. The capsule preparation may take a form of enteric coated capsule, gastric acid-resistant capsule, release-controlled capsule or the like in addition to conventional capsule preparations.

In the case of enteric coated capsule preparations, HGF coated with an enteric coating agent or HGF to which the above-mentioned suitable excipients are added is filled in a conventional capsule. Alternatively, HGF alone or HGF to which the above-mentioned suitable excipients are added may be encapsulated in an enteric coated capsule or in a capsule formed from a base material comprising an enteric polymer.

In the case of syrups, stabilizers (e.g. sodium edetate, etc.), suspending agents (e.g. gum arabic, carmellose, etc.), corrigents (e.g. simple syrup, glucose, etc.), perfumes, and the like can be appropriately selected and used.

Further, suppositories can be prepared by the conventional formulation method using a conventional suppository base (e.g. cacao butter, lauric oil, glycerogelatin, macrogol, Witepsol, etc.) and the like.

Furthermore, inhalation preparations may be produced by the conventional formulation method. In the formulation of inhalations, any additives may be used so long as they are commonly utilized for inhalation preparations. For example, in addition to propellants, the above-mentioned excipients, binders, lubricants, preservatives, stabilizers, isotonic agents, pH control agents and corrigents (e.g. citric acid, menthol, ammonium glycyrrhizate, glycine, perfume, etc.) are used. As the propellants, liquefied gas propellants, compressed gas and the like are used. The liquefied gas propellants include, for example, fluorinated hydrocarbons such as alternative chlorofluorocarbons (e.g. HCFC-22, HCFC-123, HCFC-134a, HCFC-142, etc.), liquefied petroleum ether, dimethyl ether, and the like. The compressed gas includes, for example, soluble gas (e.g. carbon dioxide gas, nitrous oxide gas, etc.) and inert gas (e.g. nitrogen gas, etc.).

Moreover, HGF used in the present invention together with a biodegradable polymer may be formulated into a delayed release preparation. In the delayed release preparations of HGF, such effects as maintenance of blood level, reduction of administration frequency, alleviation of adverse effects, etc. may be expected. Such delayed release preparations can be prepared, for example, according to the conventional method as described in Drug Delivery System, chapter 3, 1986 (published by CMC, Japan). The biodegradable polymer used in the present invention may be appropriately selected from known biodegradable polymers, and include, for example, polysaccharides (e.g. starch, dextran, chitosan, etc.), proteins (e.g. collagen, gelatin, etc.), polyamino acids (e.g. polyglutamic acid, polylysine, polyleucine, polyalanine, polymethionine, etc.), polyesters (e.g. polylactic acid, polyglycolic acid, lactic acid/glycolic acid polymer or copolymer, polycaprolactone, poly-β-hydroxybutyric acid, polymalic acid, poly-acid anhydride, fumaric acid-polyethylene glycol-vinylpyrrolidone copolymer, etc.), poly(ortho esters), polyalkyl-cyanoacrylic acids (e.g. polymethyl-α-cyanoacrylic acid, etc.), polycarbonates (e.g. polyethylene carbonate, polypropylene carbonate, etc.), among which polyesters are preferable, and polylactic acid, lactic acid/glycolic acid polymers or copolymers are more preferable. When a polylactic acid/glycolic acid polymer or copolymer is used, its component ratio (mol %) of lactic acid/glycolic acid is about 100/0 to 50/50 in case of the delayed release time of two weeks to three months, preferably two weeks to one month, though such ratio depends on the delayed release time. The average molecular weight of such polylactic acid/glycolic acid polymer or copolymer is generally 5,000 to 20,000. The polylactic acid/glycolic acid homopolymer or copolymer can be prepared according to the known method, for example, the method as described in JP-A-28521/1986. Although there is no limitation with respect to mixing ratio of HGF with biodegradable polymer, HGF is used generally in an amount about 0.01 w/w % to 30 w/w % relative to the biodegradable polymer.

HGF content in the above-mentioned preparations may be appropriately adjusted depending on dosage form, indications, degree of diseases, age, etc.

The differentiation-inducing agent of the present invention may appropriately contain other pharmaceutical active ingredients, so long as they are not contrary to the purpose of the present invention. Examples of such active ingredients include, for example, anti-cholinergic agents (e.g. ipratropium bromide, flutropium bromide, oxitropium bromide, tiotropium bromide, etc.), inhalation $\beta_2$ stimulants (e.g. fenoterol, sabutamol, formoterol, salmeterol, etc.), inhalation steroids (e.g. beclomethasone, fluticasone, budesonide, etc.), antiasthmatics (e.g. theophylline, procaterol, ketotifen, azelastine, etc.), antiallergics (e.g. ketotifen, terfenadine, azelastine, epinastine, etc.), antiinflammatory agents (e.g. diclofenac sodium, ibuprofen, indomethacin, etc.), antibiotics (e.g. cefmenoxime, cefdinir, ofloxacin, tosfloxacin, norfloxacin, etc.), antimycotics (e.g. fluconazole, itraconazole, etc.) and the like. Also, a preparation containing those pharmaceutical active ingredients may be used in combination with a preparation of the present invention. There is no limitation on those pharmaceutical active ingredients so long as the purposes of the present invention can be attained, and it is possible to use such active ingredients appropriately in a suitable mixing ratio or a combination ratio.

The differentiation-inducing agent of the present invention may be administered via a suitable administration route depending on their dosage form. For example, injections may be administered via intravenous, intraarterial, subcutaneous or intramuscular route and the like. The injection dose is usually 0.001 mg to 1000 mg on the basis of HGF, preferably 0.01 mg to 100 mg, which is appropriately administered once a day or several times a day in a divided manner, although it may be appropriately adjusted depending on the condition, age, body weight of patients, etc.

The differentiation-inducing agent of the present invention can be used to induce the differentiation of bone marrow cells into alveolar cells. As the bone marrow cells, any bone marrow cells of mammals including human beings can be used, while it is preferable to use floating bone marrow cells. For example, human bone marrow cells are harvested by the known method, suspended in a cell culture liquid, seeded in a plastic petri dish, and cultured to collect only floating cells therefrom. Subsequently, the floating bone marrow cells are cultured together with a differentiation-inducing agent of the present invention. As the cell culture liquid, a conventional culture liquid such as DMEM, MEM, RPMI1640, IMDM, etc., can be used. Although additives which are commonly used in cell culture, such as fetal bovine serum, may be added to the above-mentioned cell culture liquid, it is preferable to use a serum-free cell culture liquid in view of transplantation immunology. HGF concentration in the differentiation-inducing agent is about 1 ng/mL to about 100 ng/mL. Culture conditions are those employed in the usual cell culture, for example, at about 35° C.±2° C. in the presence of 5% carbon dioxide and the like. The bone marrow cells cultured as such are cultured for one to five weeks, resulting in differentiation into alveolar cells. The differentiation-induced alveolar cells derived from the bone marrow cells obtained as above are available as a cell for organ transplantation. To be more specific, by intravenously injecting alveolar cells differentiated and proliferated from bone marrow cells of a pulmonary emphysema patient to the patient, the transplantation into the lung can be achieved. According to this procedure, it is possible to obtain a large amount of alveolar cells needed for transplantation in pulmonary emphysema patients, from the bone marrow cells of the patients themselves.

Further, there may be another embodiment which comprises culturing bone marrow cells, utilizing the resultant proliferated non-differentiated bone marrow cells as a cell for transplantation, and administering a differentiation-inducing agent of the present invention to a recipient. According to the present invention, differentiation induction from the transplanted bone marrow cells to alveolar cells occurs effectively in the body, because a small amount of bone marrow cells harvested from a patient with pulmonary emphysema are cultured and proliferated, and a large amount of the resultant bone marrow cells are returned to the patient at the same time when a differentiation-inducing agent of the present invention is administered.

With respect to bone marrow cells to be used in the above-mentioned adoptive transfer, they are preferably those collected from the same individual to be transplanted, in view of transplantation immunology.

In recent years, gene therapies using HGF gene have been reported (see Circulation, 1997, vol. 96, No. 3459; Nature Medicine, 1999, vol. 5, p. 226-230; Circulation, 1999, vol. 100, No. 1672; Gene Therapy, 2000, vol. 7, p. 417-427), and such gene therapies have been technologically established. The present invention includes a gene therapy agent comprising introduction of HGF gene for the alveolar regeneration or formation and for induction of differentiation of bone marrow cells into alveolar cells, as well as administration of HGF as mentioned above. Hereinafter, HGF gene therapy will be described in detail.

As used herein, "HGF gene" means a gene capable of expressing HGF. To be more specific, there is exemplified a gene wherein cDNA of HGF is integrated in a suitable expression vector (nonvirus vector, virus vector) as described in non-patent literature 2; Japanese patent No. 2,777,678; Biochem. Biophys. Res. Commun., 1989, vol. 163, p.967; or Biochem. Biophys. Res. Commun., 1990, vol. 172, p. 321. Here, the base sequence of cDNA encoding HGF is described in the above literatures, and also registered in databases such as Genebank. As described in Biochem. Biophys. Res. Commun., 1989, vol. 163, p.967 the base sequence of cDNA and is as follows (SEQ ID NO: 1):

gggctcagag ccgactggct cttttaggca ctgactccga acaggattct ttcacccagg catctcctcc agagggatcc gccagcccgt ccagcagcac c atg tgg gtg acc aaa ctc ctg cca gcc ctg ctg ctg cag cat gtc ctc ctg cat ctc ctc ctg ctc ccc atc gcc atc ccc tat gca gag gga caa agg aaa aga aga aat aca att cat gaa ttc aaa aaa tca gca aag act acc cta atc aaa ata gat cca gca ctg aag ata aaa acc aaa aaa gtg aat act gca gac caa tgt gct aat aga tgt act agg aat aaa gga ctt cca ttc act tgc aag gct ttt gtt ttt gat aaa gca aga aaa caa tgc ctc tgg ttc ccc ttc aat agc atg tca agt gga gtg aaa aaa gaa ttt ggc cat gaa ttt gac ctc tat gaa aac aaa gac tac att aga aac tgc atc att ggt aaa gga cgc
agc tac aag gga aca gta tct atc act aag agt ggc atc aaa tgt cag
ccc tgg agt tcc atg ata cca cac gaa cac agc ttt ttg cct tcg agc tat
cgg ggt aaa gac cta cag gaa aac tac tgt cga aat cct cga ggg gaa
gaa ggg gga ccc tgg tgt ttc aca agc aat cca gag gta cgc tac gaa
gtc tgt gac att cct cag tgt tca gaa gtt gaa tgc atg acc tgc aat ggg
gag agt tat cga ggt ctc atg gat cat aca gaa tca ggc aag att tgt cag
cgc tgg gat cat cag aca cca cac cgg cac aaa ttc ttg cct gaa aga
tat ccc gac aag ggc ttt gat gat aat tat tgc cgc aat ccc gat ggc cag
ccg agg cca tgg tgc tat act ctt gac cct cac acc cgc tgg gag tac
tgt gca att aaa aca tgc gct gac aat act atg aat gac act gat gtt cct
ttg gaa aca act gaa tgc atc caa ggt caa gga gaa ggc tac agg ggc
act gtc aat acc att tgg aat gga att cca tgt cag cgt tgg gat tct cag
tat cct cac gag cat gac atg act cct gaa aat ttc aag tgc aag gac cta
cga gaa aat tac tgc cga aat cca gat ggg tct gaa tca ccc tgg tgt ttt
acc act gat cca aac atc cga gtt ggc tac tgc tcc caa att cca aac tgt
gat atg tca cat gga caa gat tgt tat cgt ggg aat ggc aaa aat tat atg
ggc aac tta tcc caa aca aga tct gga cta aca tgt tca atg tgg gac aag
aac atg gaa gac tta cat cgt cat atc ttc tgg gaa cca gat gca agt aag
ctg aat gag aat tac tgc cga aat cca gat gat gat gct cat gga ccc tgg
tgc tac acg gga aat cca ctc att cct tgg gat tat tgc cct att tct cgt
tgt gaa ggt gat acc aca cct aca ata gtc aat tta gac cat ccc gta ata
tct tgt gcc aaa acg aaa caa ttg cga gtt gta aat ggg att cca aca cga
aca aac ata gga tgg atg gtt agt ttg aga tac aga aat aaa cat atc tgc
gga gga tca ttg ata aag gag agt tgg gtt ctt act gca cga cag tgt ttc
cct tct cga gac ttg aaa gat tat gaa gct tgg ctt gga att cat gat gtc
cac gga aga gga gat gag aaa tgc aaa cag gtt ctc aat gtt tcc cag
ctg gta tat ggc cct gaa gga tca gat ctg gtt tta atg aag ctt gcc agg
cct gct gtc ctg gat gat ttt gtt agt acg att gat tta cct aat tat gga tgc
aca att cct gaa aag acc agt tgc agt gtt tat ggc tgg ggc tac act gga
ttg atc aac tat gat ggc cta tta cga gtg gca cat ctc tat ata atg gga
aat gag aaa tgc agc cag cat cat cga ggg aag gtg act ctg aat gag
tct gaa ata tgt gct ggg gct gaa aag att gga tca gga cca tgt gag
ggg gat tat ggt ggc cca ctt gtt tgt gag caa cat aaa atg aga atg gtt
ctt ggt gtc att gtt cct ggt cgt gga tgt gcc att cca aat cgt cct ggt
att ttt gtc cga gta gca tat tat gca aaa tgg ata cac aaa att att tta aca
tat aag gta cca cag tca tag ctgaagtaag tgtgtctgaa gcacccacca
atacaactgt cttttacatg aagatttcag agaatgtgga atttaaaatg tcactta-
caa caatcctaag acaactactg gagagtcatg tttgttgaaa ttctcattaa tgtt-
tatggg tgttttctgt tgttttgttt gtcagtgtta ttttgtcaat gttgaagtga
attaaggtac atgcaagtgt aataacatat ctcctgaaga tacttgaatg gat-
taaaaaa acacacaggt atatttgctg gatgataa Based on the above sequence data, it is therefore possible to carry out, for example, RT-PCR to mRNA from liver, etc., by use of a proper DNA segment as a PCR primer, whereby cDNA cloning of HGF is performed. Such cloning could be easily done by those skilled in the art according to fundamental textbooks such as Molecular Cloning $2^{nd}$Edit., published by Cold Spring Harbor Laboratory Press (1989). Based on the above sequence data, it is therefore possible to carry out, for example, RT-PCR to mRNA from liver, etc., by use of a proper DNA segment as a PCR primer, whereby cDNA cloning of HGF is performed. Such cloning could be easily done by those skilled in the art according to fundamental textbooks such as Molecular Cloning $2^{nd}$ Edit., published by Cold Spring Harbor Laboratory Press (1989).

Further, the HGF gene used in the present invention is not limited to the above-mentioned genes, and any HGF gene can be used as the HGF gene of the present invention so long as it expresses a protein having the substantially the same activity with that of HGF. That is, among DNAs which can hybridize with the above-mentioned cDNA under stringent conditions and DNAs encoding a protein wherein one to plural amino acids (preferably several amino acids) in the amino acid sequence encoded by the above-mentioned cDNA are substituted, deleted, added and/or inserted, any DNA encoding a protein having an activity of HGF is included in the scope of the HGF gene used in the present invention. Such DNAs can be easily obtained by common hybridization method, PCR method and the like, specifically by reference to fundamental textbooks such as Molecular Cloning mentioned above.

HGF genes used in the present invention can be applied to regeneration or formation of alveolar cells and induction of differentiation of bone marrow cells into alveolar cells, in the same manner as in the above-mentioned HGF protein.

When a gene therapy agent comprising HGF gene as an active ingredient is administered to a patient, such administration can be conducted in the conventional manner described in, for example, Basic Technology of Gene Therapy, Separate Volume of Experimental Medicine published by Yodosha, Japan, 1996; Gene Introduction and Expression Analysis Method, Separate Volume of Experimental Medicine, published by Yodosha, Japan, 1997; Gene Therapy Development Research Handbook, edited by The Japan Society of Gene Therapy, published by NTS, Japan, 1999.

The dosage form may include a variety of known forms suitable for each administration form mentioned above. DNA content in the preparation can be appropriately controlled, depending on the target disease, age and body weight of patients, etc., and usually the DNA content in accordance with the present invention is 0.0001 to 100 mg, preferably 0.001 to 10 mg.

Further, HGF gene and HGF may be used each independently or in combination.

The present invention will be illustrated by the following Examples, but it is not limited thereto. The percentage (%) means % by mass unless otherwise indicated.

EXAMPLE

Reconstitution of Bone Marrow:

Mice transgenic for enhanced green fluorescent protein (GFP) on a C57BL/6 strain background were established at Osaka University, Japan. Liver cells of fetal livers harvested from day 13.5 GFP embryos were transplanted to C57BL/6 male mice which were irradiated using doses of 12 Gy before the transplantation, according to the method by Morishita, et. al as described in Hypertension, 1999, vol. 33, p. 1379-1384. Those mice in which over 95% of the circulating white blood cells (peripheral leukocytes) were completely replaced with bone marrow cells of GFP mouse origin three weeks after the transplantation were served as recipient mice in the experiment.

Induction of Pulmonary Emphysema and Treatment

Experimental pulmonary emphysema was induced by intranasal instillation of porcine pancreas elastase into recipient mice. Three weeks after the elastase instillation, the recipient mice exhibited emphysematous changes in the lungs. At this point, the recipient mice with induced pulmonary emphysema were randomly divided into two groups, i.e. vehicle administration group and HGF administration group, which were injected intraperitoneally with a balanced diet and with HGF respectively, at a dose of 1 mg/kg once daily for 12 days.

Histological Anatomy

Lungs of the recipient mice were fixed with 4% paraformaldehyde-PBS (phosphate buffered saline) at a pressure of 20 cm $H_2O$, and paraffin sections were prepared according to the conventional method. The paraffin sections were stained with hematoxylin-eosin (HE). GFP was detected using anti-GFP antibody (Abcam, Cambridge, UK) and visualized with 3,3'-diaminobenzidine. The number of GFP-positive cells in 200 alveoli separated from each mouse was counted (each group n=5). The extent of the emphysematous lesions was assessed by measuring the mean linear intercept (hereinafter abbreviated as Lm) of alveolar septation according to the method of Thurlbeck (see Ono, M. et. al, Circulation 2002, vol. 106, p. 1-2641-269). That is, Lm of the alveolar cell in 20 visual fields randomly sampled on two slides from each mouse was measured at 400× magnification. The total distance divided by the number of alveolar intercepts gave Lm. Histological evaluations were performed blindly by three observers (K.I., T.S. and H.K.).

Immunofluorescence of the frozen sections staining was performed to identify the phenotype of the GFP-positive cells. Anti-cytokeratin 5 and 8 antibody was purchased from Chemicon (Temecula, Calif., USA), and anti-CD34 and anti-CD45 antibodies from Pharmingen (San Diego, Calif., USA).

Statistical Analysis

The data were expressed as the mean±standard error. Comparisons were made by analysis of variance, and when overall differences were identified, multiple contrasts with a Bonferroni adjustment were used to identify which groups were significantly different. Statistical significance was defined as $p<0.05$.

Results

Figure 2:
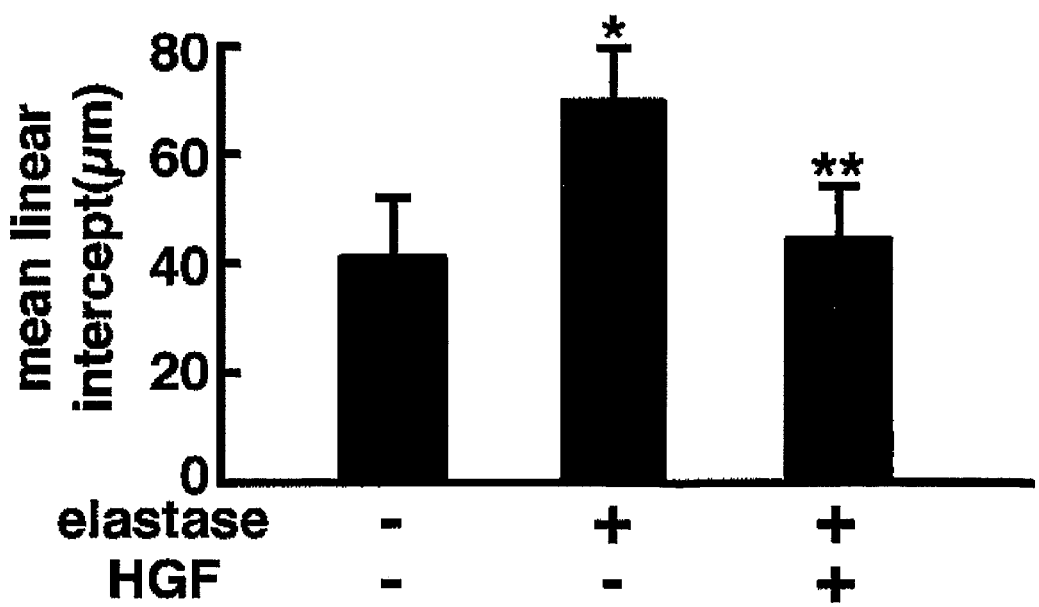
FIG. 2 shows a mean linear intercept of alveoli in pulmonary emphysema-induced recipient mice.

In the observations of tissue sections using an optical microscope, alveoli in recipient mice with elastase-induced pulmonary emphysema were destroyed, and each alveolus was enlarged about 3- to 5-fold compared to that which had not been treated with elastase. On the other hand, the alveolus in HGF administration group is almost the same with that in no elastase treatment group (see FIG. 1). The mean linear intercept in the pulmonary emphysema-induced recipient mice was shown in FIG. 2. The mean linear intercept in the recipient mice with elastase-induced pulmonary emphysema was enlarged about 1.7-fold, and that in the HGF administration group was almost the same, compared with that in no elastase treatment group.

Figure 3:
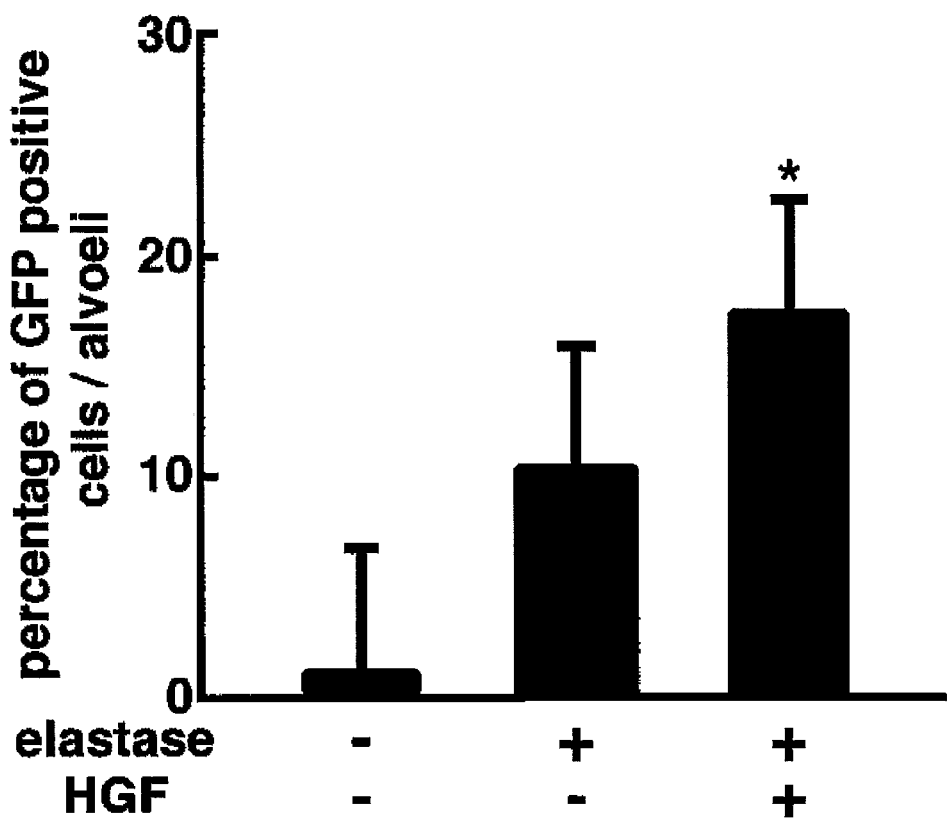
FIG. 3 shows a rate of GFP positive cells relative to alveolar cells in the lung of pulmonary emphysema-induced recipient mice.

The rate of GFP-positive alveoli relative to total alveoli in the lungs of recipient mice was shown in FIG. 3. The rate of GFP positive cells was approximately 1% in the recipient mice receiving no elastase treatment. The rate of GFP positive cells was increased approximately by 10% in the recipient mice with elastase-induced pulmonary emphysema, while that in the HGF administration group was increased approximately by 17.5%. Further, histological observation results by immunofluorescence staining revealed that such GFP positive cells were differentiated into alveolar epithelial cells and pulmonary capillary endothelial cells from GFP mice-derived bone marrow cells. These results show that HGF promotes induction of differentiation of bone marrow cells into alveoli (alveolar epithelial cells and pulmonary capillary endothelial cells, etc.).

INDUSTRIAL APPLICABILITY

The differentiation-inducing agent of the present invention induces differentiation of bone marrow cells into alveolar cells and is useful as an agent for the regeneration of alveoli destroyed due to pulmonary emphysema, etc. Also, alveolar cells differentiation-induced from bone marrow cells can be utilized as cells for transplantation in the field of regenerative medicine.

The invention claimed is:

1. A method for inducing differentiation of bone marrow cells into alveolar cells, which comprises administering an effective amount of a differentiation-inducing agent comprising recombinant hepatocyte growth factor encoded by the nucleotide sequence of SEQ ID NO: 1 by injection to a mammal having a lung disease wherein alveoli are destroyed.

2. The method according to claim 1, wherein the alveolar cells are alveolar epithelial cells.

3. The method according to claim 1, wherein the lung disease where alveoli are destroyed is selected from the group consisting of pulmonary emphysema, pulmonary fibrosis with honey-comb lung, pulmonary lymphangiomyomatosis (LAM), and destroyed lung after pulmonary resection.

4. A method for treating lung disease wherein alveoli are destroyed, which comprises administering an effective amount of a differentiation-inducing agent comprising recombinant hepatocyte growth factor encoded by the nucleotide sequence of SEQ ID NO: 1 by injection to a mammal having a lung disease wherein alveoli are destroyed, and inducing differentiation of bone marrow cells into alveolar cells.

5. The method according to claim 4, wherein the lung disease where alveoli are destroyed is selected from the group consisting of pulmonary emphysema, pulmonary fibrosis with honey-comb lung, pulmonary lymphangiomyomatosis (LAM), and destroyed lung after pulmonary resection.

6. The method according to claim 4, wherein the alveolar cells are alveolar epithelial cells.

7. A method for forming new alveoli, which comprises administering an effective amount of a differentiation-inducing agent comprising recombinant hepatocyte growth factor encoded by the nucleotide sequence of SEQ ID NO: 1 by injection to a mammal having a lung disease wherein alveoli are destroyed, and inducing differentiation of bone marrow cells into alveolar cells.

8. The method according to claim 7, wherein the lung disease where alveoli are destroyed is selected from the group consisting of pulmonary emphysema, pulmonary fibrosis with honey-comb lung, pulmonary lymphangiomyomatosis (LAM), and destroyed lung after pulmonary resection.

9. The method according to claim 7, wherein the alveolar cells are alveolar epithelial cells.

* * * * *

SEQUENCE LISTING

```
<160> NUMBER OF SEQ ID NOS: 1

<210> SEQ ID NO 1
<211> LENGTH: 2576
<212> TYPE: DNA
<213> ORGANISM: Homo Sapiens

<400> SEQUENCE: 1
gggctcagag ccgactggct cttttaggca ctgactccga acaggattct ttcacccagg    60
catctcctcc agagggatcc gccagcccgt ccagcagcac catgtgggtg accaaactcc   120
tgccagccct gctgctgcag catgtcctcc tgcatctcct cctgctcccc atcgccatcc   180
cctatgcaga gggacaaagg aaaagaagaa atacaattca tgaattcaaa aaatcagcaa   240
agactaccct aatcaaaata gatccagcac tgaagataaa aaccaaaaaa gtgaatactg   300
cagaccaatg tgctaataga tgtactagga ataaaggact tccattcact tgcaaggctt   360
ttgtttttga taaagcaaga aaacaatgcc tctggttccc cttcaatagc atgtcaagtg   420
gagtgaaaaa agaatttggc catgaatttg acctctatga aaacaaagac tacattagaa   480
actgcatcat tggtaaagga cgcagctaca agggaacagt atctatcact aagagtggca   540
tcaaatgtca gccctggagt tccatgatac cacacgaaca cagcttttg ccttcgagct   600 atcggggtaa agacctacag gaaaactact gtcgaaatcc tcgaggggaa gaaggggac   660 cctggtgttt cacaagcaat ccagaggtac gctacgaagt ctgtgacatt cctcagtgtt   720
cagaagttga atgcatgacc tgcaatgggg agagttatcg aggtctcatg gatcatacag   780
aatcaggcaa gatttgtcag cgctgggatc atcagacacc acaccggcac aaattcttgc   840
```

```
ctgaaagata tcccgacaag ggctttgatg ataattattg ccgcaatccc gatggccagc    900
cgaggccatg gtgctatact cttgaccctc acacccgctg ggagtactgt gcaattaaaa    960
catgcgctga caatactatg aatgacactg atgttccttt ggaaacaact gaatgcatcc   1020
aaggtcaagg agaaggctac aggggcactg tcaataccat ttggaatgga attccatgtc   1080
agcgttggga ttctcagtat cctcacgagc atgacatgac tcctgaaaat ttcaagtgca   1140
aggacctacg agaaaattac tgccgaaatc cagatgggtc tgaatcaccc tggtgtttta   1200
ccactgatcc aaacatccga gttggctact gctcccaaat tccaaactgt gatatgtcac   1260
atggacaaga ttgttatcgt gggaatggca aaaattatat gggcaactta tcccaaacaa   1320
gatctggact aacatgttca atgtgggaca agaacatgga agacttacat cgtcatatct   1380
tctgggaacc agatgcaagt aagctgaatg agaattactg ccgaaatcca gatgatgatg   1440
ctcatggacc ctggtgctac acgggaaatc cactcattcc ttgggattat tgccctattt   1500
ctcgttgtga aggtgatacc acacctacaa tagtcaattt agaccatccc gtaatatctt   1560
gtgccaaaac gaaacaattg cgagttgtaa atgggattcc aacacgaaca aacataggat   1620
ggatggttag tttgagatac agaaatataaac atatctgcgg aggatcattg ataaaggaga   1680
gttgggttct tactgcacga cagtgtttcc cttctcgaga cttgaaagat tatgaagctt   1740
ggcttggaat tcatgatgtc cacggaagag gagatgagaa atgcaaacag gttctcaatg   1800
tttcccagct ggtatatggc cctgaaggat cagatctggt tttaatgaag cttgccaggc   1860
ctgctgtcct ggatgatttt gttagtacga ttgatttacc taattatgga tgcacaattc   1920
ctgaaaagac cagttgcagt gtttatggct ggggctacac tggattgatc aactatgatg   1980
gcctattacg agtggcacat ctctatataa tgggaaatga gaaatgcagc cagcatcatc   2040
gagggaaggt gactctgaat gagtctgaaa tatgtgctgg ggctgaaaag attggatcag   2100
gaccatgtga gggggattat ggtggcccac ttgtttgtga gcaacataaa atgagaatgg   2160
ttcttggtgt cattgttcct ggtcgtggat gtgccattcc aaatcgtcct ggtattttg   2220 tccgagtagc atattatgca aaatggatac acaaaattat tttaacatat aaggtaccac   2280
agtcatagct gaagtaagtg tgtctgaagc acccaccaat acaactgtct tttacatgaa   2340
gatttcagag aatgtggaat ttaaaatgtc acttacaaca atcctaagac aactactgga   2400
gagtcatgtt tgttgaaatt ctcattaatg tttatgggtg ttttctgttg ttttgtttgt   2460
cagtgttatt ttgtcaatgt tgaagtgaat taaggtacat gcaagtgtaa taacatatct   2520
cctgaagata cttgaatgga ttaaaaaaac acacaggtat atttgctgga tgataa       2576
```